(12) United States Patent
Deng et al.

(10) Patent No.: US 7,170,055 B1
(45) Date of Patent: Jan. 30, 2007

(54) NANOTUBE ARRANGEMENTS AND METHODS THEREFOR

(75) Inventors: Zhifeng Deng, Palo Alto, CA (US); Erhan Yenilmez, Stanford, CA (US); Kathryn Moler, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/206,672

(22) Filed: Aug. 18, 2005

(51) Int. Cl.
G01B 9/00 (2006.01)
G01N 23/00 (2006.01)

(52) U.S. Cl. .................. 250/306; 250/307; 73/104; 73/105

(58) Field of Classification Search ........... 250/306, 250/307; 73/104, 105
See application file for complete search history.

(56) References Cited

U.S. PATENT DOCUMENTS

| | | | |
|---|---|---|---|
| 6,346,189 B1* | 2/2002 | Dai et al. .................. 205/766 |
| 6,668,628 B2* | 12/2003 | Hantschel et al. ............ 73/105 |
| 6,787,769 B2* | 9/2004 | Nakayama et al. ......... 250/306 |
| 6,818,891 B1* | 11/2004 | Hough et al. ............... 250/306 |
| 6,973,722 B2* | 12/2005 | Hantschel et al. ............ 29/874 |
| 7,040,147 B2* | 5/2006 | Chand et al. ................. 73/105 |
| 2002/0125427 A1* | 9/2002 | Chand et al. ............... 250/306 |
| 2003/0182993 A1* | 10/2003 | Hantschel et al. ............ 73/105 |
| 2004/0214177 A1* | 10/2004 | Bension ........................ 435/6 |
| 2005/0011256 A1* | 1/2005 | Hoh ............................. 73/105 |
| 2005/0102833 A1* | 5/2005 | Hantschel et al. ............ 29/874 |
| 2005/0129948 A1* | 6/2005 | Furukawa et al. .......... 428/408 |

OTHER PUBLICATIONS

Zhifeng Deng et al., "Metal-coated carbon nanotube tips for magnetic force microscopy", Appl. Phys. Lett. 85 (25), Dec. 20, 2004, pp. 6263-6265.*
Murata et al., "Exploiting Metal Coating of Carbon Nanotubes for Scanning Tunneling Microscopy Probes", Jap. J. Appl. Phys. 44 (7B), Jul. 26, 2005, pp. 5336-5338.*
NANOANDMORE USA, NanoAndMore news Jan. 27, 2006, "Nanosensors", http://www.nanoandmore.com/USA/news_doscs08.php.*
NANOANDMORE USA, "AFM Probes, tips, cantilevers", http://www.nanoandmore.com/USA/afm_probes.php.*
Sumio Iijima et al. "T. Single-shell Carbon Nanotubes of 1-nm diameter." 1993. Nature 363, pp. 603-605 (Abstract only attached).
Mildred S. Dresselhaus et al., Eds. *Carbon Nanotubes: Synthesis, Structure, Properties and Applications*. 2001. S-Verlag Berlin, Heidelberg and New York, pp. 12-25 attached.

* cited by examiner

Primary Examiner—Nikita Wells
Assistant Examiner—Bernard E. Souw (57) ABSTRACT

Nanotubes and nanotube-based devices are implemented in a variety of applications. According to an example embodiment of the present invention, nanotube tips are coated with metal. In some applications, the metal coating facilitates the resolution of nano-scale magnetic features, such as features smaller than about 20 nanometers. In another embodiment, such metal-coated nanotubes are implemented with magnetic force microscopy (MFM) applications and adapted for implementation with structures and arrangements exhibiting a high aspect ratio, facilitating quantitative analysis of MFM data.

24 Claims, 7 Drawing Sheets

NANOTUBE ARRANGEMENTS AND METHODS THEREFOR

FEDERALLY SPONSORED RESEARCH OR DEVELOPMENT

This invention was supported in part by AFOSR Grant F49620-00-1-0315, by the NSF under grant DMR-0103548, and by the DARPA-MTO Lithography Network; the U.S. Government may have certain rights in connection with this document.

RELATED PATENT DOCUMENTS

This document is related to U.S. patent application Ser. No. 10/831,786, filed on Apr. 26, 2004 and entitled "Apparatus for Making Carbon Nanotube Structure with a Catalyst Island," which is a divisional of U.S. patent application Ser. No. 10/042,426 filed on Jan. 7, 2002 and entitled "Carbon Nanotube Structure Having A Catalyst Island," now abandoned, which is a continuation-in-part of U.S. patent application Ser. No. 09/133,948 filed on Aug. 14, 1998, now U.S. Pat. No. 6,346,189, and entitled "Carbon Nanotube Structures made Using Catalyst Islands," which are all fully incorporated herein by reference.

FIELD OF THE INVENTION

The present invention relates generally to nanotube devices and more particularly to nanotubes with metal-coated tips.

BACKGROUND

Carbon nanotubes are unique carbon-based, molecular structures that exhibit interesting and useful electrical properties. Two general types of carbon nanotubes are referred to as multi-walled carbon nanotubes (MWNTs) and single-walled carbon nanotubes (SWNTs). SWNTs have a cylindrical sheet-like, one-atom-thick shell of hexagonally-arranged carbon atoms, and MWNTs are typically composed of multiple coaxial cylinders of ever-increasing diameter about a common axis. Thus, SWNTs can be considered to be the structure underlying MWNTs and also carbon nanotube ropes, which are uniquely-arranged arrays of SWNTs.

Carbon-based nanotubes are being studied for implementation in a variety of applications. These applications include, among others, chemical and bio-type sensing, field-emission sources, selective-molecule grabbing, nano-electronic devices, and a variety of composite materials with enhanced mechanical and electromechanical properties. More specifically, for example, in connection with chemical and biological detection, carbon nanotubes have been studied for applications including medical devices, environmental monitoring, medical/clinical diagnosis and biotechnology for gene mapping and drug discovery. For general information regarding carbon nanotubes, and for specific information regarding SWNTs and their applications, reference may be made generally to "Carbon Nanotubes: Synthesis, Structure, Properties and Applications," M. S. Dresselhaus, G. Dresselhaus and Ph. Avouris (Eds.), S-Verlag Berlin Heidelberg, New York, 2001; and "T. Single-shell Carbon Nanotubes of 1-nm Diameter," Iijima, S. & Ichihashi, Nature 363, 603–605 (1993).

Manufacturing processes used to make carbon nanotubes are often characterized by relatively uncontrolled carbon nanotube growth. For example, carbon nanotubes grown from catalyst material often grow in random directions. Where multiple carbon nanotubes are grown in close proximity, the carbon nanotubes often grow into contact with one another, intertwine or otherwise interact in a generally disoriented manner. This nature of grown carbon nanotubes can present challenges to using the nanotubes in a variety of applications.

Nano-magnetic materials and the shrinking bit size of magnetic recording media have increased the demand for analysis or imaging approaches providing high spatial resolution, and in some instances, increased the demand for analysis or imaging of structures exhibiting a high aspect ratio. For instance, Magnetic Force Microscopy (MFM) applications, involving a probe having a magnetic tip mounted on a cantilever, is limited in resolution by the tip's size, shape, and height above the surface of the sample being analyzed. Previously-implemented MFM probes include focused ion beam (FIB) milled sharp tips, suitable for sub-30 nm wide one dimensional features; tips with an FIB-drilled hole, suitable for imaging 50 nm transitions on a hard drive; tips with magnetic dots deposited through stencil masks, suitable for imaging features with 42 nm FWHM; and electron beam deposition (EBD) tips. Other applications have involved the use of nanotube-based MFM tips with magnetic catalyst particles to image 85 nm features; however, these approaches involving nanotube tips are generally unsuitable for topography, and the amount of magnetic material at the tip is not readily controllable.

Difficulties associated with the above discussion have presented challenges to nanotube applications, including the manufacture of nanotubes and their implementation in a variety of applications.

SUMMARY

The present invention is directed to overcoming the above-mentioned challenges and others related to nanotube devices and their implementations. The present invention is exemplified in a number of implementations and applications, some of which are summarized below.

According to an example embodiment of the present invention, a nanotube device includes a nanotube having a metal-coated tip.

In connection with another example embodiment of the present invention, a nanotube tip is coated with two or more layers, at least one of the layers including a metal material. In certain applications, the metal material is magnetic.

In another example embodiment of the present invention, a probe tip includes a base (e.g., a cantilever) with a carbon nanotube extending from a tip of the base. A fixed end of the carbon nanotube is coupled to the base, with a free end of the carbon nanotube extending away from the base tip and coated with a metal material. In some applications, the free end of the carbon nanotube is coated with magnetic metal.

In various applications, the metal material coated on the free end of the carbon nanotube includes a composition and/or a mix of layered metal suitable to the particular application for which the probe tip is to be applied. In one implementation, the free end of the carbon nanotube is coated with a first sticking layer of material adapted to couple to the carbon nanotube, with a second metal layer coated on the first sticking layer. The section metal layer includes one or more of a variety of metals, and in some instances includes a magnetic metal. In some applications, a third layer is formed over the second metal layer, and is selectively implemented to inhibit corrosion of the second metal layer. In other applications, exposed portions of the nanotube, as well as a portion of the probe tip base, are coated with metal material.

In another example embodiment of the present invention, a nanotube-based probe tip arrangement includes at least one nanotube having a fixed end coupled to a probe tip base and having a free end extending away from the probe tip base in a substantially straight direction. A sticking layer of material is coated onto the free end of the at least one nanotube, and a layer of magnetic metal material is coated onto the sticking layer. In some applications, the thickness of the magnetic material is thin (e.g., less than 20 nanometers), and the magnetic material is confined near the free end of the nanotube to mitigate interaction between samples and the fixed end of the nanotube/probe tip base. In this regard, the fixed end of the nanotube and/or the probe tip base are substantially free of the magnetic metal material.

In another example embodiment of the present invention, a probe tip arrangement is manufactured with a carbon nanotube extending from a probe tip base of a cantilever. The carbon nanotube has a fixed end coupled to the probe tip base and a free end extending away from the probe tip base. A sticking layer is coated on the free end of the carbon nanotube and adapted to couple to the carbon nanotube and a subsequently-coated layer. A magnetic layer is coated on the sticking layer, and in some applications, confined near the free end of the carbon nanotube, leaving the probe tip base substantially free of the magnetic layer.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for a variety of different types of devices, and the invention has been found to be particularly suited for nanotube-based devices and applications. While the present invention is not necessarily limited to such applications, various aspects of the invention may be appreciated through a discussion of various examples using this context.

According to an example embodiment of the present invention, carbon nanotubes are grown and coated with metal. A chemical vapor deposition (CVD) approach is implemented to grow carbon nanotubes onto probe tips, such as pyramidal silicon structures at the end of a cantilever. The resulting carbon nanotubes are optionally shortened. Once shortened (or if not shortened), a tip region of a free end of the carbon nanotubes is coated with metal. The probe tips with coated carbon nanotubes are then implemented in one or more of a variety of applications, such as tapping mode atomic force microscopy.

The wafer-scale CVD approach for growing the carbon nanotubes may involve, for example, introducing a carbon-containing gas to a catalyst on pyramidal silicon tips, with carbon depositing at the catalyst and facilitating the growth of nanotubes from the silicon tips. In one instance, a few angstroms of iron are deposited on a pyramidal silicon tip at the end of a cantilever in an e-beam metal evaporator. The cantilevers are placed inside a CVD furnace, heated up to about 900° C. in argon and a mixture of methane, ethylene and hydrogen gases are introduced to the pyramidal silicon tips for about 7 minutes. The iron particles catalyze the self-assembly of carbon nanotubes on the pyramidal silicon tips. In this context, the carbon nanotubes have a fixed end coupled to the pyramidal silicon tips, with a free end (tip) of the carbon nanotubes extending away from the pyramidal silicon tips.

A variety of nanotube types are selectively grown using the above wafer-scale approach. In some applications, carbon nanotubes grown using this approach are single-walled carbon nanotubes (SWNTs), and in other applications, carbon nanotubes grown using this approach are double-walled carbon nanotubes. The diameters of these carbon nanotubes are in the range of about 1 nm to about 5 nm, with a wide distribution of lengths and angles relative to the pyramidal silicon tip. The nanotubes protruding from the apexes of the pyramids are shortened to a few hundred nanometers using an electrical cutting approach.

Once manufactured and, where appropriate, shortened, the nanotubes are coated inside an e-beam evaporator. First, a sticking layer such as titanium is coated to the free end of each nanotube, followed by a second layer of metal such as cobalt. A protective layer such as titanium is formed on the second layer to mitigate or prevent oxidation, corrosion or other undesirable conditions. While a variety of approaches to the deposition of these coatings are implemented, some applications involve the coating of about 3 nm of titanium as the sticking layer, 7 nm of cobalt as the second layer and 3 nm of titanium as the protective layer.

The above-discussed nanotube tips are implemented in one or more of a variety of applications. In one application, a metal-coated nanotube probe tip is implemented in an MFM arrangement. Magnetic material on the nanotube tip is arranged in a narrow cylinder on the free end of the nanotube; this relatively small volume of magnetic material contributes to a signal obtained with the nanotube, facilitating relatively high spatial resolution. The sharp tip radius of the coated carbon nanotube also facilitates topographic scanning, which yields an accurate height profile for the tip to follow. The relatively small amount of magnetic material on the coated carbon nanotube tips is less invasive, in that only a small amount of magnetic material is brought into close proximity with a sample being analyzed or otherwise processed. Furthermore, modeling and analyzing implementations of the coated carbon nanotube tips is facilitated by the relatively predictable distribution of magnetic material along the carbon nanotube tip. In connection with this example embodiment, it has been discovered that by limiting the thickness and volume of the magnetic material via the sticking layer and metal layer (e.g., with e-beam evaporation) and locating the metal layer near the free end of the nanotube, interaction between the probe tip base and samples is mitigated, facilitating quantitative analysis of the samples.

For general information regarding approaches involving carbon nanotubes, and for specific information regarding approaches to coating metal onto carbon nanotube tips that may be implemented in connection with one or more example embodiments discussed herein, reference may be made to Zhifeng Deng, Yenilmez, E., Leu, J., Hoffman, J E, Straver, E W J, Hongjie Dai, Moler, K A, "Metal-coated carbon nanotube tips for magnetic force microscopy," *Applied Physics Letters* 85, 6263–5 (2004); reference may also be made to Y. Zhang and Hongjie Dai, "Formation of metal nanowires on suspended single-walled carbon nanotubes," *Applied Physics Letters* 77, 3015–17 (2000); both of these references are fully incorporated herein by reference.

Figure 1A:
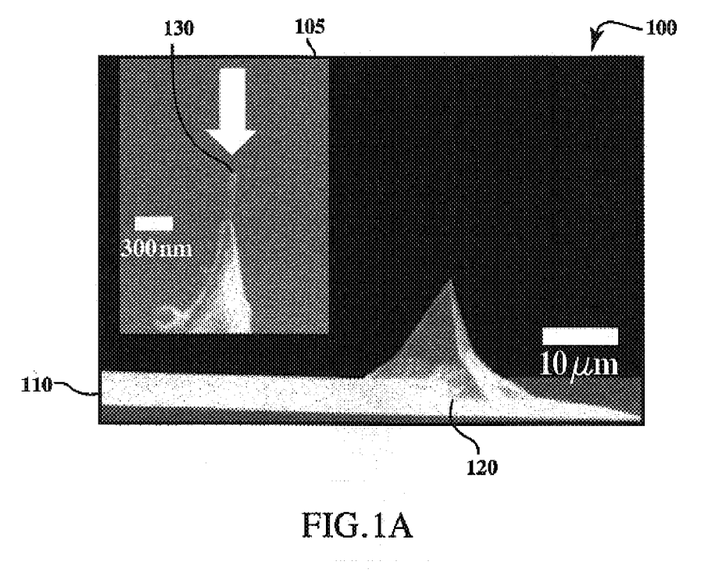
FIG. 1A shows a scanning electron microscope image of a microscopy tip arrangement, according to an example embodiment of the present invention.

Turning now to the Figures, FIG. 1A shows a scanning electron microscope (SEM) image of a MFM tip arrangement 100, according to another example embodiment of the present invention. The MFM tip arrangement includes a cantilever 110 having a silicon pyramid 120. An inset 105 at the upper left of FIG. 1A shows a high-resolution SEM image of the apex of the silicon pyramid 120, with a coated carbon nanotube (CCNT) tip 130 extending from the silicon pyramid. The CCNT tip 130 has a coating of metal near a free end (tip) portion, and in some instances, extending along the entire nanotube.

The length of the CCNT tip 130 is selected (i.e., shortened) to suit particular applications to which the MFM tip arrangement 100 is to be implemented. In connection with an example embodiment, it has been discovered that nanotubes much shorter than about 250 nm and coated with a magnetic material exhibit a resulting MFM signal having a significant contribution from the magnetic material. In this regard, various implementations involve the CCNT tip 130 at a length of about 250 nm or more to mitigate the contribution of coated magnetic material to an MFM signal obtained via the CCNT tip 130. With this approach, detrimental effects upon the magnetic spatial resolution that can be achieved with the CCNT tip 130 are mitigated.

The characteristics of the cantilever 110 are also selected to meet the particular application to which the cantilever is to be applied, by manufacturing or otherwise arranging the cantilever 110 with a selected composition and shape. In some applications, the spring constant of the cantilever 110 is about 5 N/m, its resonance frequency is about 120 kHz and its quality factor in air is about 100.

In certain manufacturing implementations, the MFM tip arrangement 100 is tested using, for example, a Tapping/Lift™ mode of Digital Instruments, Nanoscope III SPM, at room temperature and in air to map the phase shift of the cantilever while scanning a sample. Imaging parameters such as lift height and amplitude of oscillation are selected to yield the best resolution with each tip. Prior to imaging, the CCNT tip 130 is magnetized in a direction that is parallel to the CCNT using a strong permanent magnet (with no other external magnetic field applied).

Figure 1B:
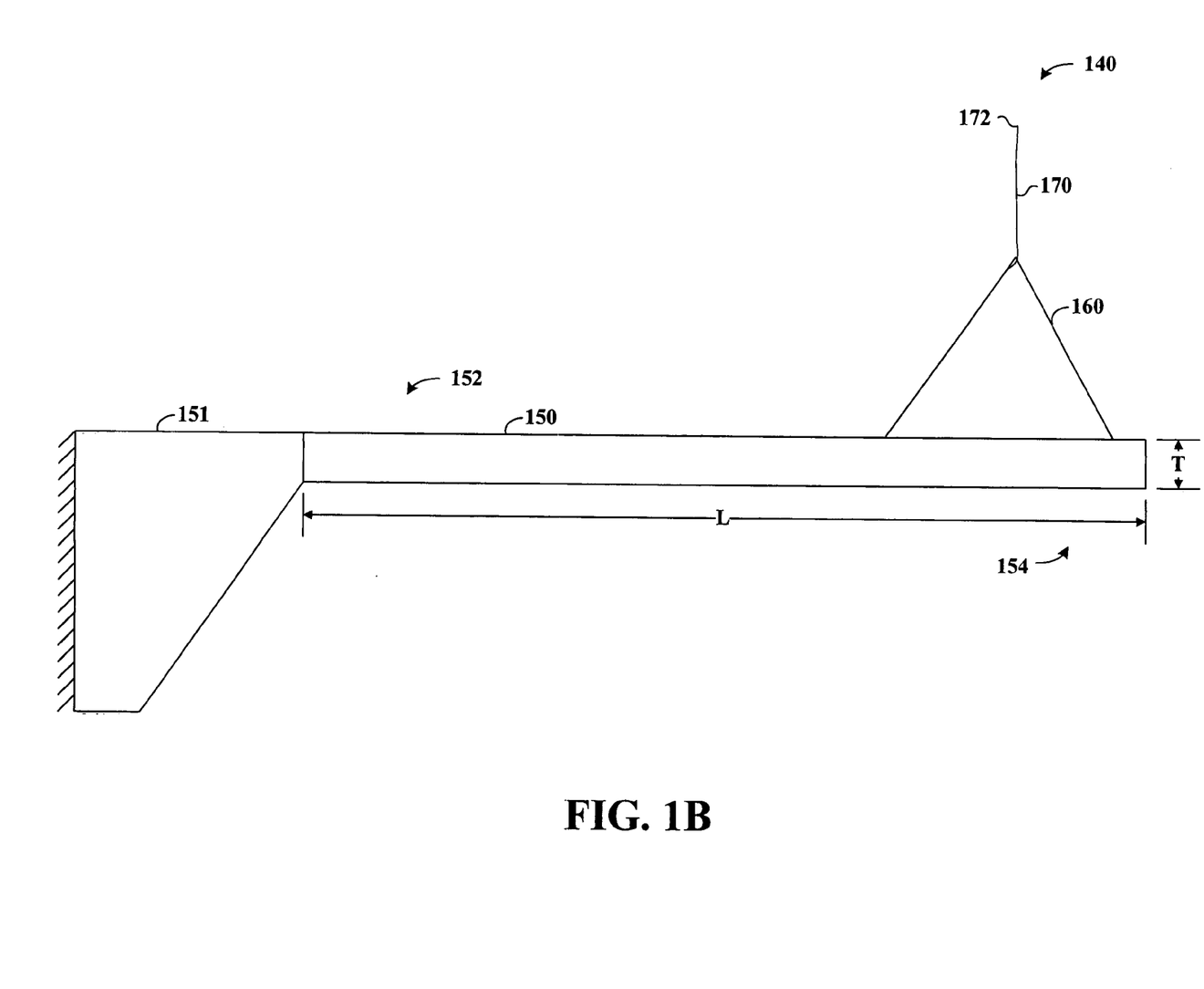
FIG. 1B shows a side view of a cantilever-tip arrangement, according to another example embodiment of the present invention.
Figure 1C:
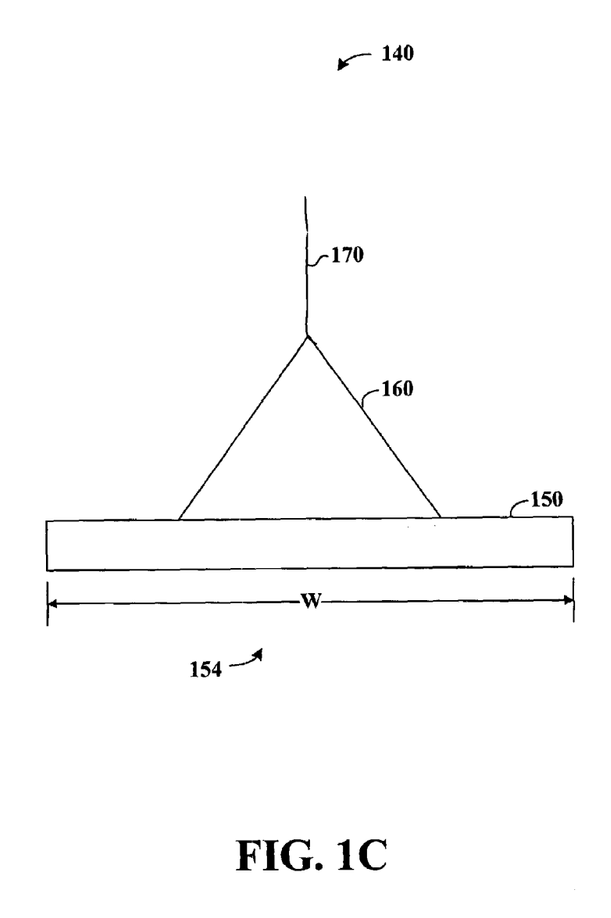
FIG. 1C shows an end view of a cantilever-tip arrangement, according to another example embodiment of the present invention.

FIG. 1B shows a side view, and FIG. 1C an end view, of a cantilever arrangement 140, according to another example embodiment of the present invention. Referring first to FIG. 1B, a cantilever 150 extends generally laterally, with a fixed end 152 and a free end 154. The fixed end 152 is coupled to a supporting arrangement 151, selectively manufactured with the cantilever 150 as a common item. A pyramidal probe tip (base) 160 extends from the cantilever 150 near the free end 154, and has a coated carbon nanotube tip 170 extending therefrom. In this regard, the pyramidal probe tip 160 is a base from which the carbon nanotube tip 170 extends, with a free end 172 of the carbon nanotube tip extending away from the pyramidal probe tip 160. A portion of the carbon nanotube tip 170 near the free end 172 is coated with metal. In some applications, the metal coating is generally confined near the free end 172 of the carbon nanotube tip 170 and in other applications, about an upper half of the carbon nanotube tip 170 including the free end 172 is coated with metal. In still other applications, all or nearly all of the carbon nanotube tip 170 is coated with metal with a portion of the metal coating selectively also coating a portion of the pyramidal probe tip 160.

Referring now to FIG. 1C, the view shows the free end 154 of the cantilever 150 with the pyramidal probe tip 160 and carbon nanotube tip 170 extending therefrom. In this regard, the cantilever 150 is generally long and rectangular, with the free end 154 able to move in a manner such as implemented with a tapping approach useful in a variety of microscopy approaches.

The materials used in the cantilever and the pyramidal probe tip 160 are selected to suit the particular application in which they are implemented. In one application, the cantilever 150 includes silicon and has a length L and thickness T (see FIG. 1B) and a width W (see FIG. 1C) that are amenable to implementation with microscopy applications, with the pyramidal probe tip 160 also including such a material and, in some applications, being of the same material as the cantilever 150.

Figure 1D:
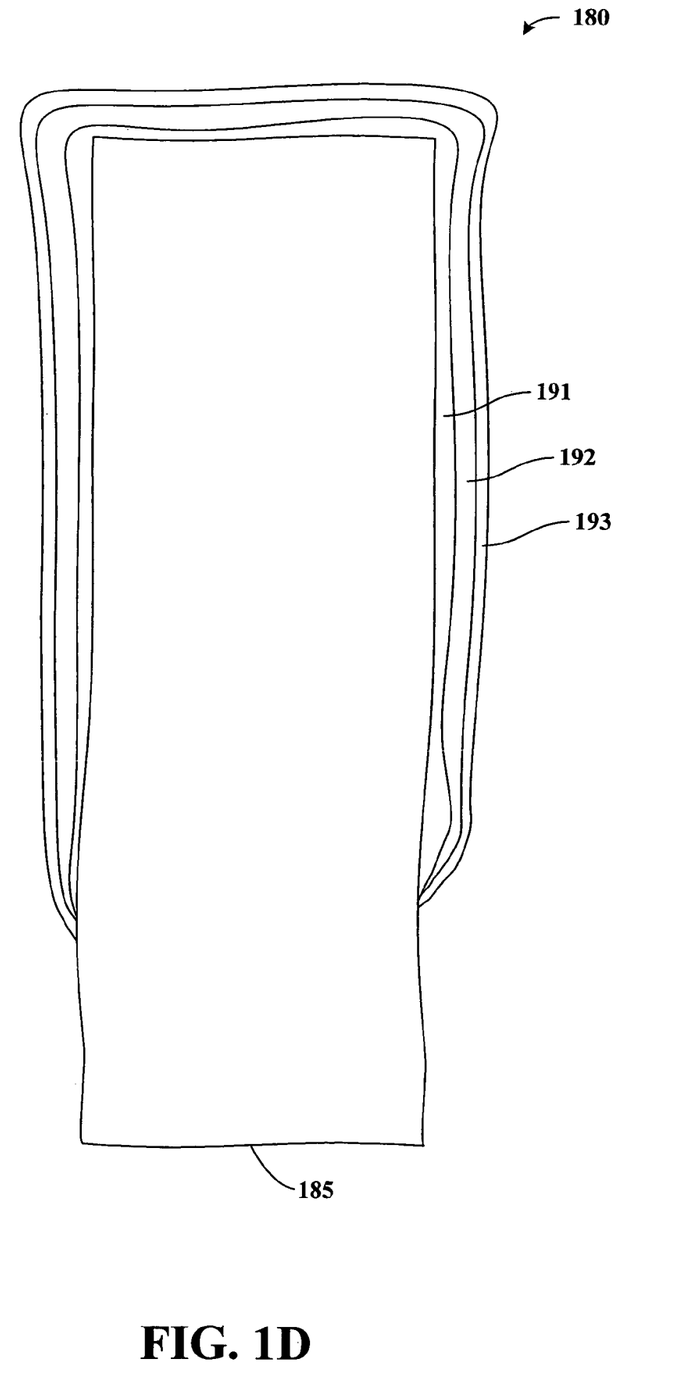
FIG. 1D shows a carbon nanotube-tip arrangement, according to another example embodiment of the present invention.

FIG. 1D shows a carbon nanotube tip arrangement 180, according to another example embodiment of the present invention. The arrangement 180 may, for example, be implemented in connection with the carbon nanotube tip 170 shown in FIGS. 1B and 1C, and implemented with a variety of applications.

The carbon nanotube tip arrangement 180 includes a carbon nanotube 185 having three layers 191, 192 and 193 formed thereon. In some applications, the carbon nanotube 185 is a SWNT, and in other applications, the carbon nanotube 185 includes more than a single wall, such as a double-walled carbon nanotube or a multi-walled carbon nanotube (MWNT).

The first layer 191 is a metal sticking layer, such as titanium, that adheres well to the carbon nanotube 185. The second layer 192 is a metal layer such as cobalt, nickel or platinum. The third layer 193 is arranged on the second layer 192 to substantially or completely cover the second layer to mitigate oxidation or other undesirable conditions with the second layer 192. Each of the layers 191–193 is formed using, for example, an e-beam approach such as that described herein.

Figure 2:
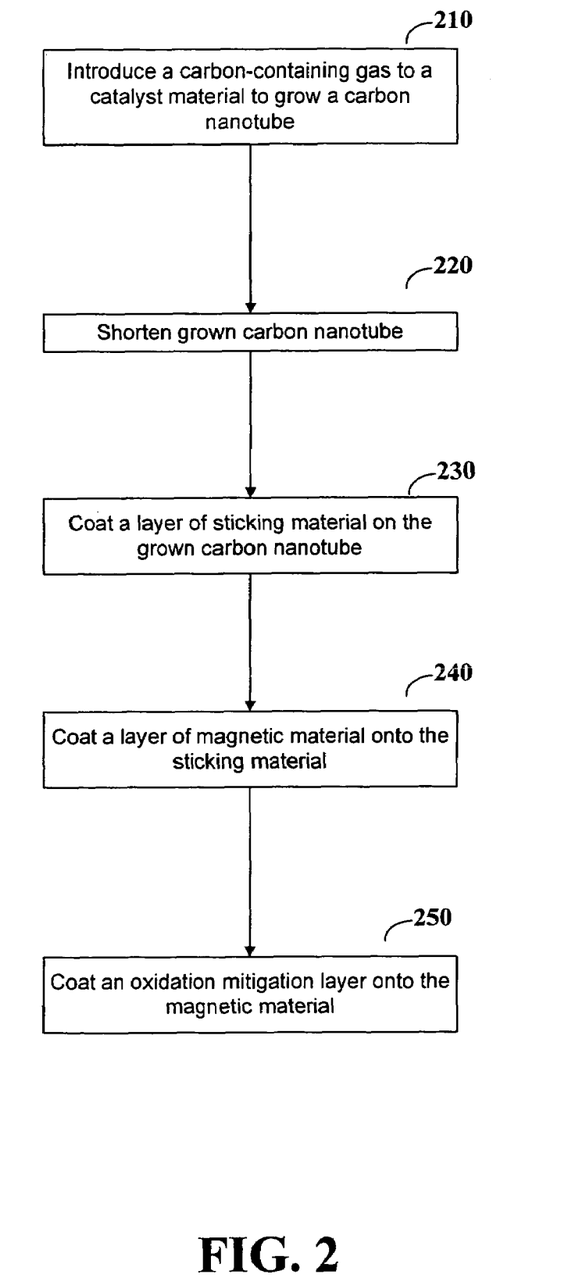
FIG. 2 is a flow diagram for an approach to manufacturing a metal-coated carbon nanotube tip, according to another example embodiment of the present invention.

FIG. 2 is a flow diagram for an approach to manufacturing a metal-coated carbon nanotube tip, according to another example embodiment of the present invention. At block 210, a carbon-containing gas is introduced to a catalyst material to grow a carbon nanotube. At block 220, the carbon nanotube is optionally shortened to a desired length (if shortening is not desired, the process moves directly to block 230 from block 210). At block 230, the carbon nanotube is coated with a sticking layer, such as titanium, that facilitates sticking (e.g., adheres) to the carbon nanotube. The sticking layer is coated with a metal (e.g., magnetic) layer such as cobalt at block 240, and the magnetic layer is coated with an oxidation mitigating material such as titanium at block 250. These coating approaches shown in blocks 230–250 are selectively carried out in an e-beam evaporator. Further, the thickness of each layer coated in blocks 230 250 is selected to meet a particular application to which the coated carbon nanotube tips are applied.

In some applications, the manufacturing approach of a metal-coated nanotube tip as described in FIG. 2 involves the formation of an array of such tips, using a thin film of iron catalyst and chemical vapor deposition on a wafer of AFM cantilevers. The cantilevers have a generally rectangular shape, with one end fixed and another end free (e.g., as shown in and discussed in connection with FIG. 1B), and with a relatively sharp pyramid at a free end of the rectangle. A focused ion beam (FIB) machine is used to direct a focused ion beam (e.g., Gallium ions) to the nanotubes to cut and shorten the nanotubes to a desirable length, as described in connection with block 220. In some applications, the FIB machine is also used to align the cut nanotubes, using one or more of the example approaches discussed herein.

After shortening, the nanotube tips in the array are coated with a sticking layer as described in block 230, followed by another metal such as Cobalt, Nickel or Platinum in an e-beam evaporator, as described in block 240. A crystal thickness monitor in the e-beam evaporator is used to control the nominal thickness of the coating or coatings; that is, when the coating reaches a desirable thickness as detected via the monitor, the e-beam evaporator is controlled to stop the application of the coating. Where oxidation or other contamination is desirably mitigated, the nanotubes in the array are also coated with an oxidation mitigation material as described in connection with block 250.

Figure 3:
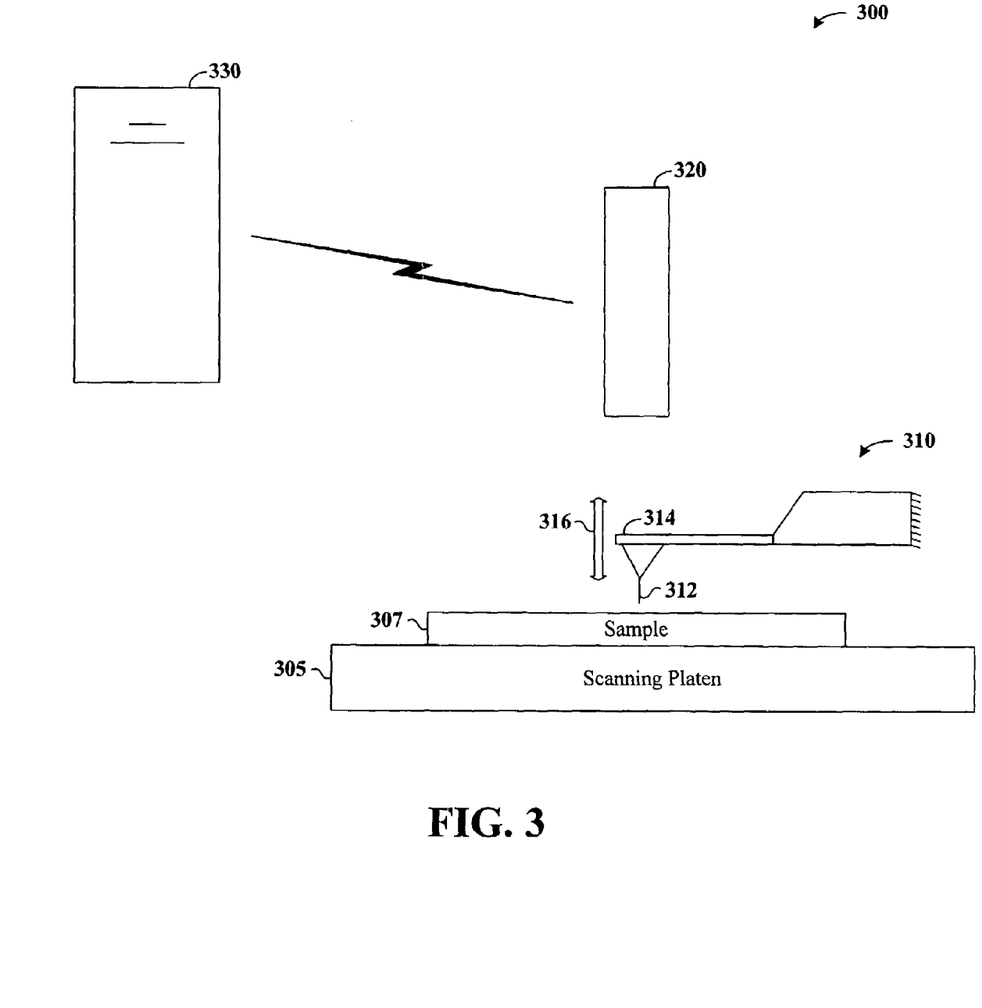
FIG. 3 is a magnetic force microscopy arrangement, according to another example embodiment of the present invention.

As discussed above, the coated nanotube approaches discussed herein are applicable to a variety of applications. FIG. 3 shows one such application, where a coated carbon nanotube is implemented with a magnetic force microscopy arrangement 300, according to another example embodiment of the present invention.

FIG. 3 shows a magnetic force microscopy (MFM) arrangement 300 employing a metal-coated carbon nanotube tip, according to another example embodiment of the present invention. The MFM arrangement 300 includes a scanning platen 305 that holds a specimen such as sample 307 in place for analysis. A coated carbon nanotube cantilever arrangement 310 is arranged over the sample 307 and scanning platen 305 in a manner that facilitates movement of a coated carbon nanotube probe tip 312 over the sample in a tapping mode, with a free end 314 of the cantilever moving relative to the sample as represented by bidirectional arrow 316.

The coated carbon nanotube probe tip 312 is coated with magnetic metal in a manner such as discussed in connection with the figures above. In some applications, the cantilever arrangement 310 is implemented using approaches similar to that shown in and described using connection with FIGS. 1A–1D. The magnetic metal coated carbon nanotube probe tip 312 is arranged relative to the sample 307 such that magnetic forces or force gradients associated with the sample 307 act on the probe tip 312 and effect a displacement of the free end 314 of the cantilever arrangement 310.

A displacement detection arrangement 320, such as a microscope arrangement, is arranged over the free end 314 of the cantilever arrangement 310 and adapted to detect movement of the free end. Data characterizing the detected movement is communicated from the displacement detection arrangement 320 to a computer 330, which processes the data for analysis. The processed data is used to provide an output such as an image or processed data that can be used to analyze the sample 307.

The cantilever arrangement 310 is operated with the scanning platen 305 in a number of manners, depending upon the application and desired analysis approach. A force image associated with the sample 307 is obtained by detecting the static deflection of the free end 314, and a force gradient image associated with the sample 307 is obtained by detecting a resonance frequency change of the free end when the free end is oscillated (e.g., in the direction of bidirectional arrow 316). The relatively thin magnetic metal coating of the carbon nanotube probe tip 312 facilitates such analysis, in particular where the sample 307 exhibits relatively high aspect ratio surface characteristics, or otherwise benefits from a sharp (small diameter) magnetic probe tip MFM application.

Figure 4:
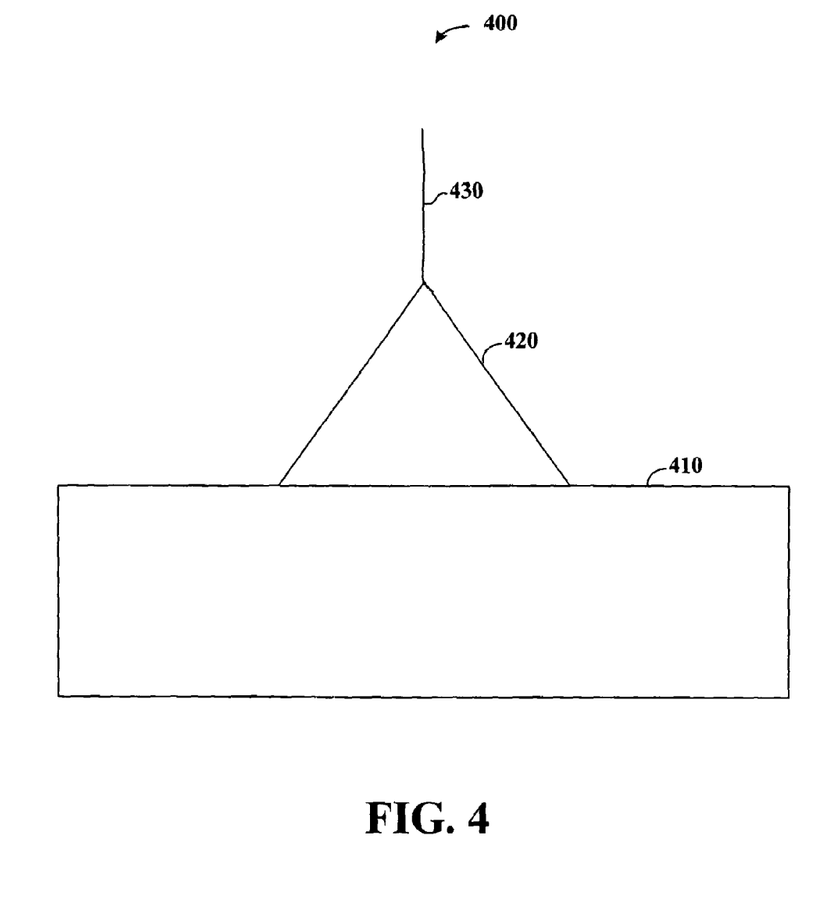
FIG. 4 shows a nanotube field emitter arrangement, according to another example embodiment of the present invention.

FIG. 4 shows a nanotube field emitter arrangement 400, according to another example embodiment of the present invention. The field emitter arrangement 400 includes a pyramidal tip 420 on a substrate 410, such as a silicon wafer. A coated carbon nanotube 430 extends from the pyramidal tip, with a lower end of the coated carbon nanotube coupled to the pyramidal tip 420 and an upper end of the carbon nanotube free. The coated carbon nanotube includes a sticking layer and a metal layer, such as the sticking and metal layers 191 and 192 shown in FIG. 1D, with the metal layer arranged with the carbon nanotube to couple to an electrode-type arrangement to emit an electric field. In some applications, the field emitter arrangement 400 is formed in an array of the pyramidal tips with carbon nanotubes extending therefrom. For general information regarding field emission devices and for specific information regarding approaches to field emission with carbon nanotubes in which various example embodiments of the present invention can be applied, reference can be made to "Carbon Nanotubes: Synthesis, Structure, Properties and Applications" at pages 371–373, referenced hereinabove.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include modifying the nanotubes for particular applications, altering nanotube-based circuit arrangements, using materials in addition to carbon in nanotubes, such as boron, interchanging nanotube films and single nanotubes, and where appropriate, using SWNTs as building blocks for more complex devices. Such modifications and changes do not depart from the true spirit and scope of the present invention, which is set forth in the following claims.

What is claimed is:
1. A nanotube-based tip arrangement comprising:
a tip base;

at least one nanotube having a fixed end coupled to the tip base and having a free end extending away from the tip base;

a sticking layer of material coated onto the free end of the at least one nanotube; and a layer of metal material coated onto the sticking layer.

2. The arrangement of claim 1, wherein the sticking layer and the layer of metal are e-beam evaporated layers having a thickness of less than about 10 nanometers.

3. The arrangement of claim 1, wherein the tip base is a probe tip base coupled to a free end of a cantilever.

4. The arrangement of claim 1, wherein at least a portion of the tip base is coated with the sticking layer.

5. The arrangement of claim 4, wherein at least a portion of the sticking layer on the tip base is coated with the metal material.

6. The arrangement of claim 1, further comprising a protective layer coated onto the layer of metal material.

7. The arrangement of claim 6, wherein the protective layer is adapted to mitigate oxidation of the layer of material.

8. The arrangement of claim 6, wherein
the sticking layer of metal is about 3 nanometers thick,
the layer of metal is magnetic metal at about 7 nanometers in thickness, and
the protective layer is a metal layer at about 3 nanometers thick.

9. The arrangement of claim 1, wherein the nanotube extends in a substantially straight arrangement from the fixed end to the free end thereof, and wherein the fixed end of the nanotube is substantially free of the layer of metal material.

10. The arrangement of claim 1, wherein the nanotube is a carbon nanotube.

11. The arrangement of claim 1, wherein the nanotube is a single-walled carbon nanotube.

12. The arrangement of claim 1, wherein the nanotube is a double-walled carbon nanotube.

13. The arrangement of claim 1, wherein the nanotube is a multi-walled carbon nanotube.

14. The arrangement of claim 1, wherein the tip base is coupled to a free end of a magnetic force microscopy cantilever and wherein the layer of metal material is a magnetic material.

15. The arrangement of claim 1, wherein the at least one nanotube is a field emission device.

16. A magnetic force microscopy arrangement comprising:
a cantilever having a fixed end and a free end;
a pyramidal tip base coupled to the free end of the cantilever;
a carbon nanotube probe tip having a fixed end coupled to the pyramidal tip base and a free end extending away from the pyramidal tip base;

a sticking layer of metal coated onto the free end of the carbon nanotube; and a magnetic layer coated onto the sticking layer.

17. The arrangement of claim 16, further comprising a protective layer coated onto the magnetic layer.

18. The arrangement of claim 16, further comprising:
a sample holder arranged adjacent to the cantilever and adapted to hold a sample in proximity to the carbon nanotube probe tip;
a sensing arrangement adapted to detect movement of the free end of the cantilever in response to interaction between the magnetic layer and the sample, and to pass data characterizing the detected movement; and
a computer arrangement adapted to receive the data from the sensing arrangement and to provide an output, corresponding to the received data, which characterizes the sample.

19. A method for manufacturing a probe tip arrangement having a carbon nanotube extending from a probe tip base of a cantilever, the carbon nanotube having a fixed end coupled to the probe tip base and having a free end extending away from the probe tip base, the method comprising:
coating a sticking layer on the free end of the carbon nanotube, the sticking layer adapted to couple to the carbon nanotube and a subsequently-coated layer; and
coating a magnetic layer on the sticking layer.

20. The method of claim 19, further comprising coating a protective layer on the magnetic layer, the protective layer adapted to mitigate contamination of the magnetic layer.

21. The method of claim 19, wherein coating at least one of the sticking layer and the magnetic layer includes electron-beam evaporating the at least one layer.

22. The method of claim 19, further comprising:
providing the carbon nanotube with its fixed end coupled to the probe tip base, the provided carbon nanotube extending in a substantially straight arrangement from the fixed end to the free end thereof.

23. The method of claim 19, wherein coating a magnetic layer on the sticking layer includes coating a layer of magnetic metal on the carbon nanotube at the free end thereof and having a thickness that is less than about 10 nanometers, wherein the fixed end of the carbon nanotube is not coated with the layer of magnetic material.

24. A field emitter arrangement comprising:
a pyramidal base;
a carbon nanotube field emission tip having a fixed end coupled to the pyramidal base and a free end extending away from the pyramidal base;
a sticking layer of metal coated onto the free end of the carbon nanotube; and
a metal layer coated onto the sticking layer.

* * * * *

UNITED STATES PATENT AND TRADEMARK OFFICE
CERTIFICATE OF CORRECTION

PATENT NO.      : 7,170,055 B1                                    Page 1 of 1
APPLICATION NO. : 11/206672
DATED           : January 30, 2007
INVENTOR(S)     : Deng et al.

It is certified that error appears in the above-identified patent and that said Letters Patent is hereby corrected as shown below:

Col. 7, line 16: "230 250" should read --230-250--.

Signed and Sealed this

First Day of May, 2007

JON W. DUDAS
*Director of the United States Patent and Trademark Office*